United States Patent [19]

Giray et al.

[11] Patent Number: 4,705,867

[45] Date of Patent: Nov. 10, 1987

[54] PROCESS FOR THE PRODUCTION OF 1,2-DITHIOLAN-3-PENTANOIC ACID (THIOCTIC ACID) AND INTERMEDIATE COMPOUNDS THEREFOR

[75] Inventors: Guenes Giray, Kleinostheim; Klaus Huthmacher, Gelnhausen; Axel Kleemann, Mühlheim; Thomas Lied, Obertshausen, all of Fed. Rep. of Germany

[73] Assignee: Degussa Aktiengesellschaft, Frankfurt am Main, Fed. Rep. of Germany

[21] Appl. No.: 848,212

[22] Filed: Apr. 4, 1986

[30] Foreign Application Priority Data

Apr. 11, 1985 [DE] Fed. Rep. of Germany ....... 3512911

[51] Int. Cl.$^4$ .......................................... C07D 339/04
[52] U.S. Cl. ....................................... 549/39; 562/503; 562/508; 562/518; 562/577
[58] Field of Search .................. 549/39; 562/503, 508, 562/518, 577

[56] References Cited

U.S. PATENT DOCUMENTS

| | | | |
|---|---|---|---|
| 2,752,373 | 6/1956 | Acker | 549/39 |
| 2,752,374 | 6/1956 | Acker | 549/39 |
| 2,792,406 | 5/1957 | Acker | 549/39 |
| 2,980,716 | 4/1961 | Reed | 549/39 |
| 3,049,549 | 8/1962 | Reed | 549/39 |
| 3,223,712 | 12/1965 | Ose et al. | 549/39 |

FOREIGN PATENT DOCUMENTS 0762575 11/1956 United Kingdom ................... 549/39

OTHER PUBLICATIONS

Reed, J. Amer. Chem. Soc., vol. 77, pp. 416–419 (1955).
Bullock, J. Amer. Chem. Soc., vol. 79, pp. 1978–1982 (1957).

Primary Examiner—Henry R. Jiles
Assistant Examiner—J. G. Mullins
Attorney, Agent, or Firm—Cushman, Darby & Cushman

[57] ABSTRACT

1,2-Dithiolane-3-pentanoic acid (D,L-thioctic acid) of the formula

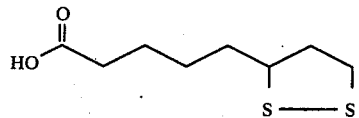

IX is prepared by a process comprising (a) reacting a 2-(3-alkylthiopropionyl)-cyclopentanone-1 of the formula

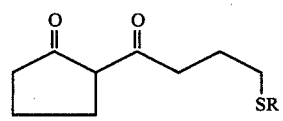

V where R is a $C_1$–$C_4$ alkyl, phenyl or benzyl in aqueous alkaline solution at a temperature of about 20° C. to about 90° C. to form the corresponding carboxylic acid of formula VI

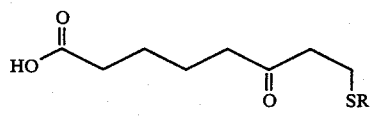

VI (b) reacting the compound of formula with an alkyl mercaptan at a temperature between −20° C. and 0° C. to form the corresponding thioketal of formula VII

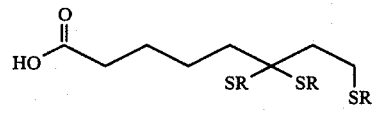

VII (c) reacting the compound of formula VII with sodium in liquid ammonia at a temperature between −60° C. and −10° C. to form the 6,8-dimercaptooctanoic acid of formula VIII (Abstract continued on next page.)

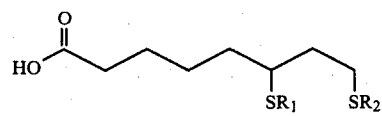

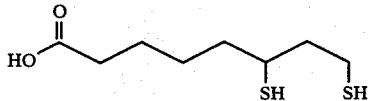

(d) reacting the 6,8-dimercaptooctanoic acid of formula VIII in alkaline solution with an iron (III) salt and oxygen to form the 1,2-dithiolane-3-pentanoic acid of formula IX, or in place of steps (a) through (c) reacting an acid of formula XII where $R_1$ and $R_2$ are hydrogen, $C_1$–$C_4$-alkyl, phenyl or benzyl, with the proviso that both $R_1$ and $R_2$ cannot be benzyl, with sodium in liquid ammonia at a temperature between $-60°$ C. and $-10°$ C. to form the corresponding 6,8-dimercaptooctanoic acid of formula VIII. The compounds of formulae VI, VII, XII are new.

5 Claims, 2 Drawing Figures

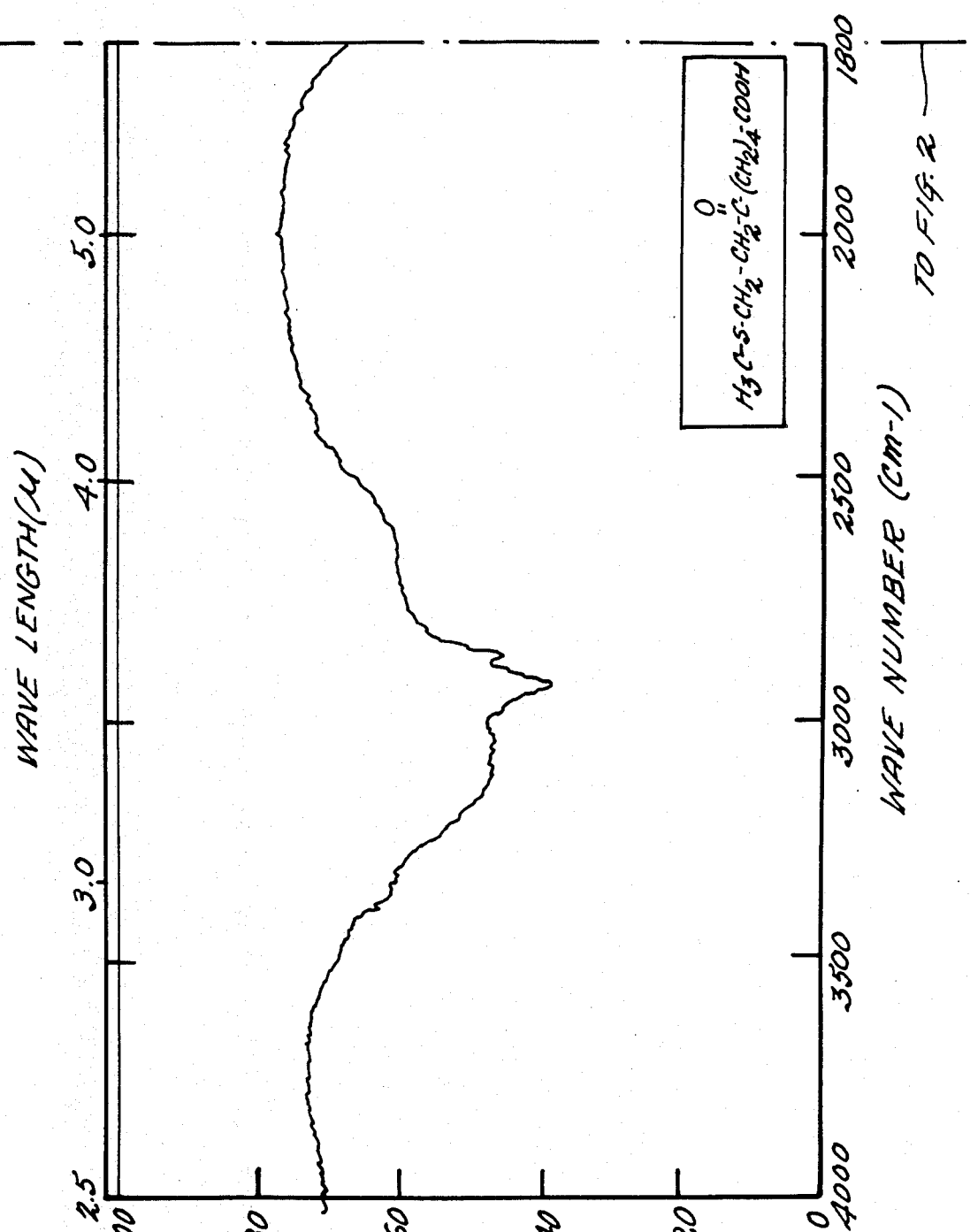

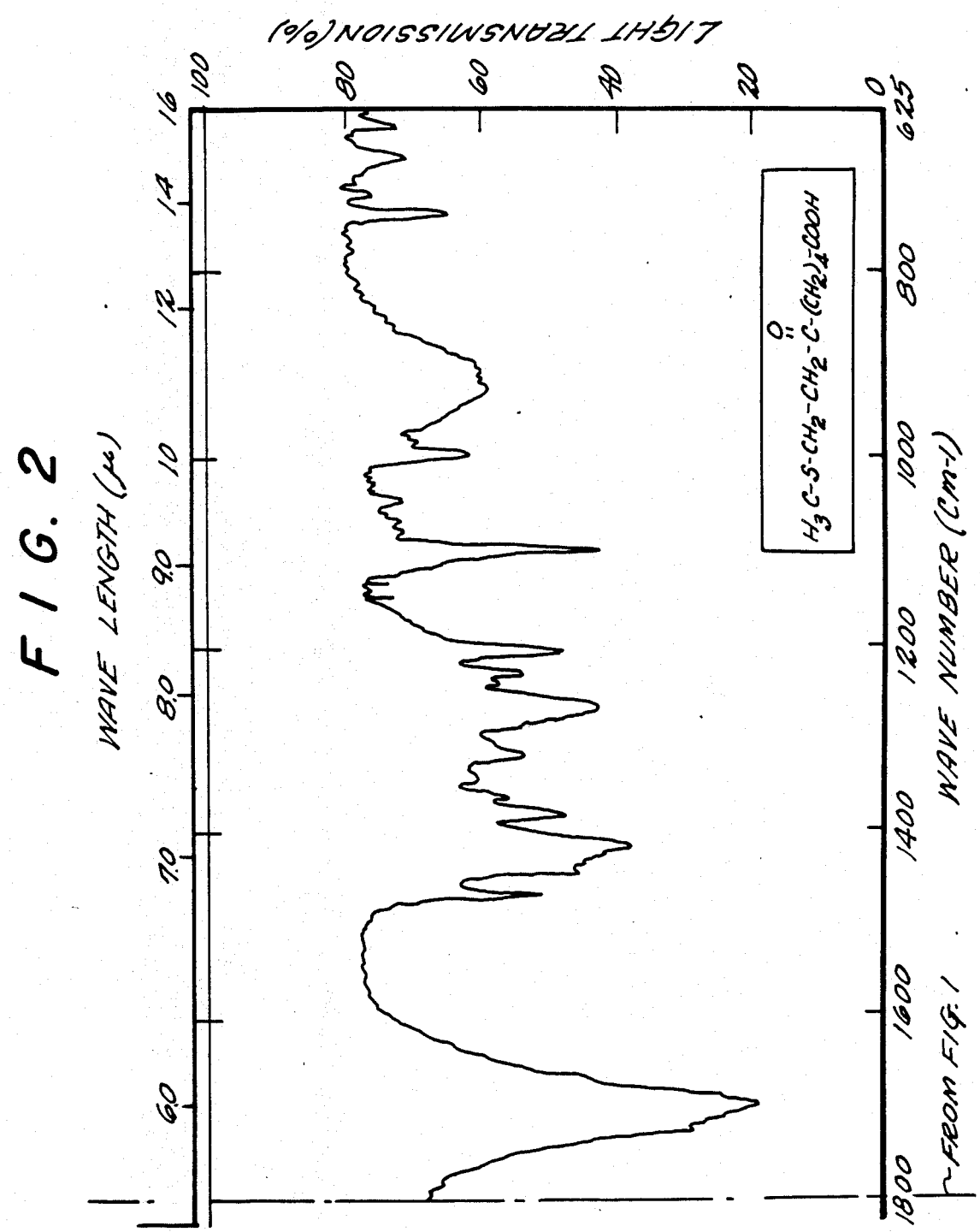

PROCESS FOR THE PRODUCTION OF 1,2-DITHIOLAN-3-PENTANOIC ACID (THIOCTIC ACID) AND INTERMEDIATE COMPOUNDS THEREFOR

BACKGROUND OF THE INVENTION

The invention is directed to a new, improved process for the production of 1,2-dithiolane-3-pentanoic acid (thioctic acid, α-lipoic acid). Thioctic acid was produced for the first time in crystalline form from liver extract in 1953 by the American biochemist L. J. Reed and J. C. Gunsalus. The optically active (+)-α-lipoic acid is a natural material which occurs in slight concentration in animals as well as in the humans. Lipoic acid acts as one of several coenzymes in the oxidative decarboxylation of pyruvate and other α-ketocarboxylic acids. It belongs to the materials which favorably influence the parenchyma damage of the liver (necotropic materials). D,L-thioctic acid is employed as a pharmaceutical preparative for the treatment of acute and chronic liver illnesses as well as poisonings. In the treatment of illnesses which require a high dosage of chemotherapy which heavily burden the liver, thioctic acid supports the regeneration of the liver. A further area of use for thioctic acid is in the treatment of neuropathy.

There are several multi-step syntheses known for the production of thioctic acid, which are described for example in Acker U.S. Pat. No. 2,752,373; Acker U.S. Pat. No. 2,752,374; Acker U.S. Pat. No. 2,792,406; Reed U.S. Pat. No. 2,980,716; Reed U.S. Pat. No. 3,049,549; and Ose U.S. Pat. No. 3,223,712. Most of the known syntheses for thioctic acid are based on the reaction of 5-chloro-carbonylvaleric acid methyl ester (1) with ethylene (2) in the presence of aluminum chloride. The 8-chloro-6-oxo-octanoic acid methyl ester (3) formed thereby is then converted in various ways into thioctic acid.

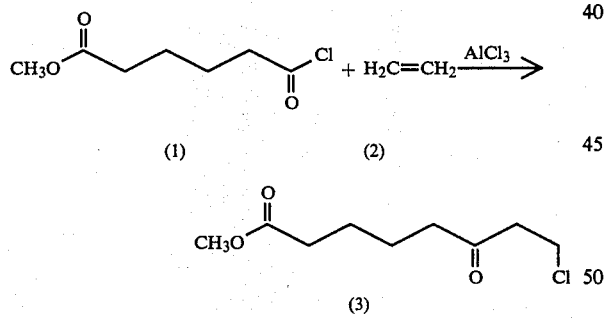

The synthesis of L. J. Reed and C. J. Nui in J. Amer. Chem. Soc., Volume 77, pages 416-419 (1955) starting from the intermediate step (3) using very corrosive phosphorus tribromide leads to thioctic acid with a modest total yield of 17% based on the acid chloride (1). Starting from the acid chloride (1) according to Reed U.S. Pat. No. 2,980,716 there is obtained a better total yield through a multi-step process, clearly the industrial realizability of this synthesis is limited because of the large number of vacuum distillations necessary. A further synthesis of thioctic acid is described by M. W. Bullock et al. in J. Amer. Chem. Soc., Volume 79, pages 1978-1982 (1957) starting from the 8-chloro-6-oxo-octanoic acid methyl ester (3) via the introduction of the sulfur atom into the molecule by means of a special cobalt polysulfide catalyst and hydrogen sulfide. This method of synthesis is not interesting industrially since the catalyst cannot be completely regenerated and besides it is necessary to operate at quite high pressures.

In Acker U.S. Pat. No. 2,792,406 there is described the production of thioctic acid by the reaction of 6,8-dichloro-octanoic acid esters with sodium sulfide and sulfur. Hereby first the chlorine is exchanged with disodium disulfide formed from sodium sulfide and sulfur, subsequently the ester is saponified and then acidified. A significant disadvantage of this process is the formation of polymeric thioctic acid which can only be separated with difficulty and only incompletely so that there is a pure thioctic acid obtained only in low yield. The entire disclosures of the patents and two literature articles mentioned above are hereby incorporated by reference and relied upon.

In spite of the numerous known syntheses for thioctic acid there is a need for an economical synthesis with a high yield. The present invention is directed to a process for the production of thioctic acid from readily available starting materials which are reacted in simple chemical operations without drastic conditions. The synthesis shows a very good yield of 47% of theory via 8 steps.

SUMMARY OF THE INVENTION

The new process for the production of thioctic acid is described as follows wherein in the stated formulae R is always $C_1$-$C_4$-alkyl, e.g. methyl, ethyl, propyl, isopropyl, butyl, or sec. butyl, phenyl or benzyl:

1. Reaction of an alkyl mercaptan with an acrylic acid alkyl ester is known manner to form a 3-alkylthio-propionic acid alkyl ester.

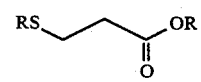

2. Reaction of a 3-alkylthiopropionic acid alkyl ester with an alkali hydroxide, e.g. sodium hydroxide, potassium hydroxide, in known manner to form a 3-alkyl-thiopropionic acid.

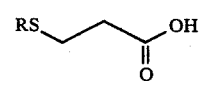

3. Reaction of 3-alkylthiopropionic acid (II) with a chlorinating agent, such as, e.g. thionyl chloride, phosphorus trichloride, phosphorus pentachloride, in known manner to form a 3-alkylthiopropionic acid chloride.

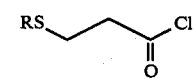

4. Production of an enamine from cyclopentanone with a secondary amine, such as e.g. morpholine, piperidine, pyrrolidine, oxazolidine, N-methyl piperazine in known manner to form a 1-(dialkylamino)-cyclopentene-1 (IV) wherein $R_{11}$ and $R_{12}$ indicate a ring having —$CH_2$—$CH_2$—O—$CH_2$—$CH_2$ or —$(CH_2)_5$—, —$(CH_2)_4$—, —$CH_2$—$CH_2$—$OCH_2$—, —$CH_2$—$CH_2$—N($CH_3$)—$CH_2$—$CH_2$—

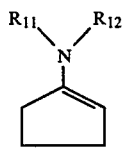

5. Reaction of 3-alkylthiopropionic acid chloride (III) with an enamine of cyclopentanone (IV) in known manner to form a 2-(3-alkyl-thiopropionyl)-cyclopentane-1-one

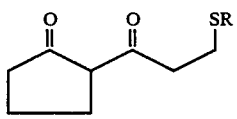

6. Reaction of a 2-(3-alkylthiopropionyl)-cyclopentan-1-one (V) with an equimolar or excess amount of an alkali hydroxide, such as e.g. sodium hydroxide or potassium hydroxide, in water at a temperature of about 20° C. up to about 90° C., preferably from 50° C. to 80° C., especially at 70° C. to 75° C. and subsequently acidifying with a customary acid, such as e.g. hydrochloric acid (or sulfuric acid) to a neutral or slightly acid pH to form an 8-alkylthio-6-oxooctanoic acid.

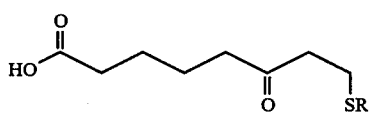

7. Reaction of an 8-alkylthio-6-oxooctanoic acid (VI) with a 4 to 6 fold molar excess of a $C_1$–$C_4$-alkyl mercaptan in the presence of a hydrohalic acid, such as e.g. hydrogen chloride or hydrogen bromide and a small amount of an acidic inorganic salt, such as e.g. zinc chloride, zinc bromide, boron trichloride, boron trifluoride, with or without a solvent at a temperature between −20° C. and 0° C., preferably between −10° C. and 0° C., especially between −5° C. and 0° C. to form the 6,6,8-trialkylthioctanoic acid.

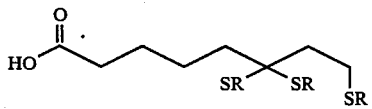

8. Reaction of a 6,6,8-trialkylthiooctanoic acid (VII) with a 6 to 10 fold molar excess of sodium in liquid ammonia and an inert organic solvent such as e.g. aliphatic symmetrical or asymmetrical ethers having $C_1$–$C_5$-alkyl groups, as well as cyclic ethers, especially dimethyl ether, diethyl ether, methyl tertiary butyl ether, di-n-butyl ether (also diamyl ether, dioxane or tetrahydrofuran) at a temperature between −60° C. and −10° C., preferably between −50° C. and −35° C., especially between 45° C. and −35° C. to form 6,8-dimercaptooctanoic acid.

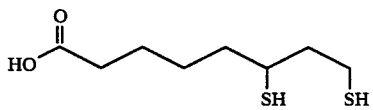

9. Reaction of the 6,8-dimercaptooctanoic acid (VIII) with an about equimolar amount of alkali hydroxide, such as e.g. sodium hydroxide or potassium hydroxide, in water at a pH of about 9 with an iron (III) salt, such as e.g. iron (III) sulfate (or iron (III) chloride) and oxygen according to a known method to form the 1,2-dithiolan-3-pentanoic acid (thioctic acid).

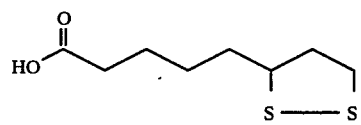

or instead of the steps 6 to 8.

10. Reaction of an acid (XII) wherein $R_1$ and $R_2$ are $C_1$–$C_4$-alkyl, phenyl, benzyl, or hydrogen with a 5 to 8 fold molar excess of sodium in liquid ammonia and an inert organic solvent, such as e.g. aliphatic symmetrical or asymmetrical ethers having $C_1$–$C_5$-alkyl groups, as well as cyclic ethers, especially dimethyl ether, diethyl ether, methyl tertiary butyl ether di-n-butyl ether, at a temperature between −60° C. and −10° C., preferably between −45° C. and −35° C. to form the corresponding 6,8-dimercaptooctanoic acid (VIII).

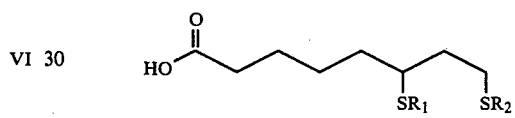

The acid of formula (XII) can be formed for example starting from 8-alkylthio-6-oxooctanoic acid of formula (VI) in known manner via the ester (VIa), the 6-hydroxy derivative (VIb) and via the 6-halo derivative (X) wherein $R_3$ is chlorine or bromine.

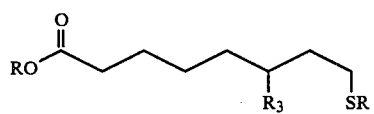

and (a) reacting with sodium benzylthiolate in alcoholic solution at a temperature between 0° C. and 80° C., preferably between 50° C. and 80° C., especially between 75° C. and 80° C. and subsequently reacting with aqueous alkali hydroxide at 80° C. to 100° C. or (b) by reacting with a 0.5 to 2 molar amount of sodium sulfide and sulfur in alcoholic solution at a temperature between 0° C. and 80° C., preferably between 50° C. and 80° C., especially between 75° C. and 80° C., subsequently reacting with a 2 to 4-fold molar amount of alkali hydroxides, such as e.g. sodium hydroxide or potassium hydroxide, in water at 80° C. to 100° C. and subsequently reducing with a 0.5 to 1 molar amount of sodium borohydride.

The production of the acid having formula (XII) for example also can be carried out by reaction of 6-acetylthio-8-alkylthiooctanoic acid ethyl ester of formula (XI) producible in known manner from the 6-halogen derivative of formula (X) by reaction with alkali hydroxide in alcoholic-aqueous solution at a temperature between 20° C. and 80° C., preferably between 50° C. and 70° C., especially between 60° C. and 65° C.

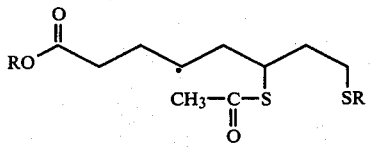

XI

The new process of production leads to the racemic form of the thioctic acid (IX). An optically active, pure enantiomeric form of the thioctic acid can be obtained from the racemic D,L-thioctic acid by resolution of the racemate in known manner by means of fractional crystallization.

The process can comprise, consist essentially of or consist of the stated steps with the recited materials.

Unless otherwise indicated all parts and percentages are by weight.

DESCRIPTION OF THE DRAWINGS

FIGS. 1 and 2 together are the IR spectrum of 8-methylthio-6-oxooctanoic acid.

DETAILED DESCRIPTION

Example 1

Production of 3-methylthiopropionic

Acid Ethyl Ester (I)

245 grams (5.1 moles) of methyl mercaptan were led into 750 ml of acetone at 0° C., 2.5 grams of Triton B added and there were slowly dropped in at 0° C. 500 grams (5.8 moles) of methyl acrylate. The mixture was allowed to warm up to room temperature within 10 hours and the excess methyl acrylate and acetone distilled off. There were obtained 645 grams (95% of theory) of 3-methylthiopropionic acid methyl ester having a boiling point of 75° C. at 17 mbar.

Example 2

Production of 3-Methylthiopropionic Acid (II)

432.0 grams (3.22 moles) of 3-methylthiopropionic acid methyl ester were stirred into a solution of 240.0 grams (6 moles) of sodium hydroxide in 960 ml of water and subsequently the mixture was heated for 1.5 hours with stirring at reflux. The reaction mixture was cooled to 10° C. and acidified with concentrated hydrochloric acid to pH 1 and the phases separated. After extraction of the aqueous phase with dichloromethane the combined organic phases were dried with sodium sulfate. After distilling off the solvent there were obtained 375 grams (97% of theory) of DC homogeneous 3-methylthiopropionic acid, which was further used as crude product. Boiling point: 127° to 130° C. at 14 mbar.

Example 3

Production of 3-Methylthiopropionic

Acid Chloride (III)

745.0 grams (6 moles) of 3-methylthiopropionic acid were dropped into 952.0 grams (8 moles) of thionyl chloride at room temperature, whereupon the reaction was cooled. Subsequently stirring was carried out for 1 hour at 20° C. and 3 hours at 50° C. to 60° C. Excess thionyl chloride was distilled off at normal pressure and hereupon there were obtained by fractional distillation 730.0 grams (88% of theory) of 3-methylthiopropionic acid chloride having a boiling point of 73° C. to 76° C. at 14 mbar.

Example 4

Production of 1-(Morpholin-4yl)-Cyclopent-1-ene (IV)

The process was carried out according to the directions of S. Hunig and W. Lendle; Chem. Ber. Volume 93, pages 909 et seq. (1960)

A solution of 84.0 grams (1 mole) of cyclopentanone and 130.5 grams (1.5 moles) of morpholine in 400 ml of toluene was heated at reflux for 4 hours at the water trap. The morpholine and toluene were distilled off and the residue fractionated in a vacuum. There were obtained 135 grams (88% of theory) of 1-(morpholin-4yl)-cyclopentene-1 having a boiling point of 105° C. to 109° C. at 18 mbar.

Example 5

Production of
2-(3-Methylthiopropionyl)-Cyclopentan-1-one V 170.0 grams (1.23 moles) of 3-methylthiopropionic acid chloride in 100 ml of dichlormethane at 0° C. were slowly (2.5 hours) dropped into a solution of 183.6 grams (1.2 moles) of 1-(morpholin-4-yl)-cyclopent-1-ene and 121.2 grams (1.2 moles) of triethylamine in 1200 ml of dichloromethane. After completion of the addition, stirring was continued for 1 hour at +10° C. and 2 hours at +20° C. and the precipitated triethylamine hydrochloride filtered off. The filtrate was treated with 130 ml of concentrated hydrochloric acid, as well as 380 ml of water and stirred vigorously for 10 hours at 30° C. Then the phases were separated and the organic phase was washed with water and saturated sodium bicarbonate solution. After drying with magnesium sulfate and distilling off the solvent there were obtained 220.0 grams (98% of theory) of crude 2-(3-methylthio-propionyl)-cyclopentan-1-one which can be employed in the next step. By fractional vacuum distillation of the crude product there were obtained 166.1 grams (74% of theory) of pure diketone as a light yellow oil having a boiling point of 120° C. to 135° C. at 0.5 mbar.

Example 6

Production of 8-Methylthio-6-Oxooctanoic Acid (VI)

387.0 grams (2.08 moles) of crude 2-(3-methylthiio-propionyl)-cyclopentane-1-one were stirred into a solution of 88.0 grams (2.2 moles) of sodium hydroxide in 1600 ml of water and the mixture heated for 3 hours at 70° C. to 75° C. The reaction mixture cooled to +5° C. was acidified with concentrated hydrochloric acid, the organic phase separated off and the aqueous phase extracted with dichloromethane. The combined organic phases were dried with sodium sulfate and concentrated in a vacuum. There were obtained 415 grams (98% of theory) of a semi-crystalline crude product which after recrystallization from diethyl ether gave 280 grams (69% of theory) pure, crystalline 8-methylthio-6-oxooctanoic acid having a melting point of 50° C. to 52° C.

$^1$H-NMR 60 MHz (CDCl$_3$): δ=1.45–1.95 (m, 4H); 2.15 (s, 3H); 2.25–2.8 (m, 4H); 2.82 (s, 4H); 10.03 ppm (s, 1H).

IR (KBr): ν=2500–3500 (m), 2935 (m), 1695 cm$^{-1}$ (s)
C$_9$H$_{16}$O$_3$S

| | % C | % H | % S |
|---|---|---|---|
| Calculated: | 52.94 | 7.84 | 15.69 |
| Found: | 53.21 | 8.02 | 14.96 |

Example 7
Production of 6,6,8-Trimethylthiooctanoic Acid (VII)

At −10° C. 2.5 grams (0.02 mole) of zinc chloride were added to a mixture of 129.97 grams (2.70 moles) of methyl mercaptan and 127.0 grams (0.62 mole) of 8-methylthio-6-oxooctanoic acid and for 2 hours there was led in a weak stream of dry hydrogen chloride. Thereby the temperature of the reaction mixture was held to 0° C. to +5° C. by cooling. After ending the introductin of hydrogen chloride stirring was continued for 2 hours at 0° C. and the mixture allowed to stand for 10 hours at 0° C. Excess methyl mercaptan was distilled off, the residue taken up in 200 ml of water and after 0.5 hours extracted twice, each time with 200 ml of dichloromethane. The combined extracts were washed with 100 ml of water, dried with sodium sulfate and the solvent distilled off. There were obtained 173.0 grams (98% of theory) of crude 6,6,8-trimethylthiooctanoic acid as a yellow oil.

$^1$H-NMR 60 MHz (CDCl$_3$): δ=1.3 -2.1 (m, 8H); 2.03 (s, 6H); 2.11 (s, 3H); 2.15-3.85 (m, 4H); 11.0 ppm (s, 1H).

IR (Film): ν=3000-3450 (b, s) 2920 (s,), 2860 (s), 2450-2750 (b, m), 1700 cm$^{-1}$ (s)

| | % C | % H | % S |
|---|---|---|---|
| Calculated: | 46.77 | 7.85 | 34.05 |
| Found: | 46.77 | 7.85 | 32.66 |

Example 8
Production of 6,8-Dimercaptooctanoic Acid (VIII)

26.0 grams (0.092 mole) of 6,6,8-trimethyl-thiooctanoic acid in 150 ml of diethyl ether were introduced (0.3 hours) into 400 ml of ammonia at −50° C., the mixture warmed to −40° C. and 18.0 grams (0.780 mole) of sodium added in small portions. Stirring was carried out for 2 hours, the mixture cooled again to −50° C.; excess sodium reacted by addition of ammonium chloride and the ammonia distilled off. The residue was taken up in 200 ml of water and slowly acidified with 10% hydrochloric acid. The methyl mercaptan formed thereby was carried out with a stream of nitrogen and condensed in a cooling trap. The aqueous solution was extracted twice each time with 15 ml of diethyl ether, the combined extracts dried with sodium sulfate and the solvent removed in a vacuum. There were obtained 18.3 grams (96% of theory) of 6,8-dimercaptooctanoic acid as a light yellow oil.

Example 9
Production of D,L-Thioctic Acid (IX)

8.0 grams (0.038 mole) of 6,8-dimercapto octanoic acid were added to 1.54 grams (0.038 mole) of sodium hydroxide in 90 ml of water and the solution formed adjusted to pH 9 with dilute aqueous sodium hydroxide. The solution was extracted twice, each time with 30 ml of methyl tertiary butyl ether, the aqueous solution separated off and the residual ether removed in a vacuum. The solution was diluted with 200 ml of water, 7 mg of iron (III) sulfate added and oxygen led in with stirring at room temperture. After 2.5 hours the reaction solution had reached a pH of 12.4, the supply of oxygen was ended and the precipitated iron salt filtered off. The clear yellow solution was acidified with 10% hydrochloric acid at 5° C., to 10° C., further stirred for 1 hour at pH 1 and the precipitated crude product filtered off. The precipitate was washed with water, dried in a vacuum and recrystallized from ethyl acetate/hexane. After drying there were obtained 5.9 grams (75% of theory) of 1,2-dithiolane-3-pentanoic acid as yellow crystals having a melting point of 61° C. to 62° C.

$^1$H-NMR 60 MHz (CDCl$_3$): δ=1.3–2.30 (m, 8H); 2.15–2.80 (m, 2H); 3.18 (t, J=7Hz, 2H); 3.3–3.85 (m, 1H); 11.3 ppm (s, 1H).

IR (KBr): ν3000-3250 (b, m) 2935 (s), 2865 (m), 2250-2800 (b, m), 1690 cm$^{-1}$ (s).

| | % C | % H | % S |
|---|---|---|---|
| Calculated: | 46.57 | 6.84 | 31.08 |
| Found: | 46.46 | 6.70 | 30.77 |

Example 10
Productin of 8-Methylthio-6-oxooctanoic Acid Ethyl Ester (VIa)

26 grams of concentrated sulfuric acid were added to a solution of 130.0 grams (0.64 mole) of 8-methylthio-6-oxooctanoic acid in 250 ml of ethanol and the mixture heated for 4 hours at reflux. Then excess ethanol was distilled off, the residue treated with 400 ml of water and neutralized with solid sodium carbonate. After multiple extractions with dichloromethane the combined extracts were washed with water, dried with sodium sulfate and the solvent removed in a vacuum. There remained behind 142.0 grams (95% of theory) of crude product which was suited for the following reaction. After vacuum distillation there were obtained 123.0 grams (83% of theory) of 8-methylthio-6-oxooctanoic acid as a colorless oil having a boiling point of 125° C. to 132°C. at 1 mbar.

Example 11
Production of 6-Hydroxy-8-Methylthiooctanoic Acid Ethyl Ester (VIb)

18.0 grams (0.47 mole) of sodium borohydride in 100 ml of water were dropped into a solution of 207.0 grams (0.9 mole) of 8-methylthio-6-oxooctanoic acid (VIa) in 150 ml of ethanol at +5° C. Subsequently stirring was carried out for 1 hour at +10° C. and 2 hours at +25° C. After acidification with dilute hydrochloric acid the ethanol was distilled off, 300 ml of water added and the mixture extracted with dichloromethane. The combined extracts were washed twice, each time with 100 ml of water, dried with sodium sulfate and concentrated in a vacuum. After fractional distillation there were obtained 178.3 grams (85% of theory) of 6-hydroxy-8-methylthiooctanoic acid ethyl ester as a colorless oil having a boiling point of 152° C. at 0.5 mbar.

Example 12
Production of 6-Chloro-8-Methylthiooctanoic Acid Ethyl ester (X) R$_3$=Chlorine 89.25 grams (0.7 mole) of thionyl chloride at +5° C. were slowly dropped into a solution of 137.0 grams (0.59 mole) of 6-hydroxy-8-methylthiooctanoic acid ethyl ester (VIb) and 1 ml of pyridine in 300 ml of dichloromethane. After stirring for 1 hour at +10° C. the mixture was heated for 3 hours at reflux and subsequently concentrated in a vacuum. The residue was treated with 200 ml of water and extracted with dichloromethane. After drying the combined extracts with sodium sulfate the solvent was removed in a vacuum. By fractional distillation there were obtained 125.1 grams (84% of theory) of 6-chloro-8-methylthiooctanoic acid ethyl ester as a colorless oil having a boiling point of 135° C. to 145° C. at 1 mbar.

Example 13a

Productin of 6-Benzylthio-8-Methylthiooctanoic Acid (XII) $R_1=CH_2-CH_2-CH_5H_6$, $R_2=CH_3$ 12.4 grams (0.1 mole) of benzyl mercaptan were added to a solution of 2.3 grams of sodium in 75 ml of water free ethanol (corresponding to 0.1 mole of sodium ethanolate) and the mixture stirred for 0.5 hour at +10° C. Thereupon there were added 22.72 grams (0.09 mole) of 6-chloro-8-methylthiooctanoic acid ethyl ester (X) and the mixture heated for 20 hours at reflux. To the cooled reaction mixture there were added 11.2 grams (0.17 mole) of potassium hydroxide and stirring was carried out for 20 hours at room temperature. After addition of 500 ml of water the mixture was acidified with dilute hydrochloric acid, extracted with dichloromethane, the combined extracts washed with saturated aqueous sodium chloride solution and dried with sodium sulfate. By distilling off the solvent in a vacuum there were obtained 28.0 grams (96% of theory) of crude b 6-benzylthio-8-methylthiooctanoic acid.

$^1$H-NMR 60 MHz (CDCl$_3$): $\delta=1.1$–2.0 (m, 8H); 2.06 (s, 3H); 2.05–3.0 (m, 5H); 3.69 (m, 2H); 7.3 (s, 5H); 11.3 ppm (s, 1H).

Example 13b

Production of 6-Mercapto-8-Methylthiooctanoic Acid (XII) $R_1=H$, $R_2=CH_3$ 72.0 grams (0.31 mole) of 6-chloro-8-methylthiooctanoic acid ethyl ester (X) were quickly added at +70° C. to a solution of 25.6 grams (0.2 mole) of sodium sulfide and 6.4 grams (0.2 mole) of sulfur in a mixture of 250 ml of ethanol and 20 ml of water and the mixture heated to reflux for 6 hours. Subsequently there were added 20.0 grams (0.5 mole) of sodium hydroxide in 200 ml of water, the mixture heated at reflux for 3 hours and a part of the ethanol distilled off. To the cooled residue there were added 25 grams (0.62 mole) of sodium hydroxide in 60 ml of water as well as 8 grams (0.21 mole) of sodium borohydride in 70 ml of water. This mixture was allowed to stand for 1 hour at room temperature and stirred for 3 hours at reflux, as well as standing for an additional 10 hours at room temperature.

Thereupon the mixture was acidified with concentrated hydrochloric acid, extracted with dichloromethane, the combined extracts washed with saturated sodium bicarbonate solution, dried with sodium sulfate and concentrated in a vacuum. There were obtained 54 grams (78% of theory) of 6-mercapto-8-methylthiooctanoic acid as a yellow oil having a boiling point of 150° C. to 170° C. at 0.5 mbar.

$^1$H-NMR 60 MHz (CDCl$_3$); $\delta=1.36$ (d, J=7Hz, 1H); 1.30–1.95 (m, 8H); 2.08 (s, 3H); 2.0–3.15 (m, 5H); 11.3 ppm (s, 1H).

Example 14

Production of 6-Bromo-8-Methylthiooctanoic Acid Ethyl Ester (X) $R_3=$Bromine 64.8 grams (0.24 mole) of phosphorus tribromide at 0° C. were dropped into a solution of 140.0 grams (0.6 mole) of 6-hydroxy-8-methylthiooctanoic acid ethyl ester (VIb) in 150 ml of tetrachloromethane, the mixture stirred for 2 hours at 0° C. and allowed to stand for 10 hours at room temperature. There were dropped into the reaction mixture, cooled to 0° C., 150 ml of water and subsequently 600 ml of diethyl ether. The organic phase was separated off, washed with saturated aqueous sodium bicarbonate solution, dried with sodium sulfate and the solvent removed in a vacuum. After vacuum distillation of the residue there were obtained 135.0 grams (76% of theory) of 6-bromo-8-methylthiooctanoic acid ethyl ester as a yellowish oil having a boiling point of 140° C. to 145° C. at 1 mbar.

Example 15

Production of 6-Acetylthio-8-Methylthiooctanoic Acid Ethyl Ester (XI)

8.6 grams (0.113 mole) of thioacetic acid in 20 ml of water-free ethanol were neutralized to phenolphthalein with 81 ml of 10% ethanolic potash solution (0.113 mole potassium hydroxide) and 29.7 grams (0.1 mole) of 6-bromo-8-methylthiooctanoic acid ethyl ester added. The mixture was heated at reflux for 6 hours in a nitrogen atmosphere and allowed to stand for 10 hours at room temperature. The precipitated potassium bromide was filtered off, the filtrate concentrated in a vacuum, the residue taken up in 300 ml of diethyl ether and filtered, the filtrate was washed twice, each time with 100 ml of water, dried with sodium sulfate and concentrated in a vacuum. There were obtained 26 grams (89% of theory) of crude 6-acetylthio-8-methylthiooctanoic acid ethyl ester.

Example 16

Productin of 6-Mercapto-8-Methylthiooctanoic Acid (XII) $R_1=H$, $R_2=CH_3$ 11.9 grams (40.7 mmoles) of 6-acetylthio-8-methylthiooctanoic acid ethyl ester (XI) were added to a solution of 7.5 grams (133.7 mmoles) of potassium hydroxide in 100 ml of methanol and 5 ml of water and the mixture heated at reflux for 10 hours under a cover of nitrogen. After a further 10 hours at room temperature the solvent was removed in a vacuum, the residue taken up on 100 ml of 3N hydrochloric acid and extracted three times, each time with 100 ml of ethyl acetate. After drying the combined extracts with magnesium sulfate the solvent was removed in a vacuum. The short path distillation of the residue gave 7.1 grams (78% of theory) of 6-mercapto-8-methylthiooctanoic acidas a pale yellow oil having a boiling point of 150° C. to 170° C. at 0.5 mbar.

Example 17

Production of 6,8-Dimercaptooctanoic Acid (VIII)

(a) 9.0 grams (0.040 mole) of 6-mercapto-8-methylthiooctanoic acid (XII) in 50 ml of diethyl ether were slowly (1 hour) dropped into a solution of 2.0 grams (0.087 mole) of sodium in 200 ml of ammonia at −50° C. Subsequently there were added a further 3.0 grams (0.130 mole) of sodium portionwise, further stirring carried out for 2 hours at −50° C. and the mixture allowed to stand for 10 hours at −35° C. Excess sodium was reacted by the additon of solid ammonium chloride, ammonia distilled off and the residue taken up in 100 ml of water. The aqueous mixture was acidified with semi-concentrated hydrochloric acid, extracted three times, each time with 100 ml of diethyl ether, the combined extracts dried with magnesium sulfate and the solvent removed in a vacuum. There remained behind 8.0 grams (95% of theory) of crude 6,8-dimercaptooctanoic acid. (b) 28.0 grams (0.087 mole) of 6-benzylthio-8-methylthiooctanoic acid (XII) in 70 ml of diethyl ether were slowly (1 hour) dropped into a sodium of 6.0 grams (0.26 mole) of sodium in 400 ml of ammonia at −50° C. After decoloration of the solution a further 4.0 gram (0.17 mole) of sodium were added in small pieces, stirring carried out for 2 hours at −50° C. and the mixture allowed to stand for 10 hours at −40° C. Excess sodium was reacted by addition of solid ammonium choride, ammonia distilled off and the residue taken up in 150 ml of water. The mixture was acidified with semi-concentrated hydrochloric acid, extracted three times, each time with 150 ml of diethyl ether, the combined extracts dried with magnesium sulfate and the solvent removed in a vacuum. The short path distillation of the crude product gave 14.7 grams (81% of theory) of 6,8-dimercaptooctanoic acid as a yellow oil having a boiling point of 146° C. to 152° C. at 0.5 mbar.

The entire disclosure of German priority application No. P 3512911.5 is hereby incorporated by reference.

What is claimed is:

1. A process for preparing thioctic acid of the formula

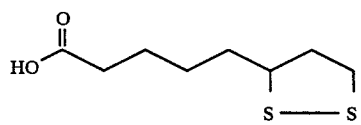

comprising (a) reacting a 2-(3-alkylthiopropionyl)-cyclopentan-1-one of the formula

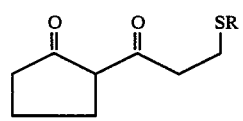

where R is a $C_1$–$C_4$ alkyl, phenyl or benzyl in aqueous alkaline solution at a temperature of about 20° C. to about 90° C. to form the corresponding carboxylic acid of formula VI

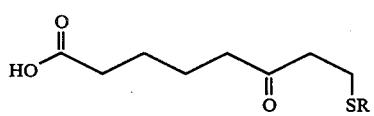

(b) reacting the compound of formula VI with an alkyl mercaptan at a temperature between −20° C. and 0° C. to form the corresponding thioketal of formula VII

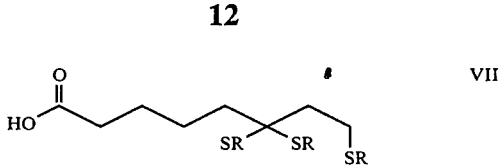

(c) reacting the compound of formula VII with sodium in liquid ammonia at a temperature between −60° C. and −10° C. to form the 6,8-dimercaptooctanoic acid of formula VIII

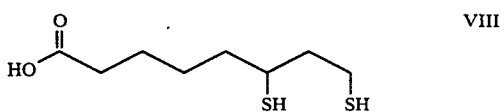

(d) reacting the 6,8-dimercaptooctanoic acid of formula VIII in alkaline solution with an iron (III) salt and oxygen to form the thioctic acid of formula IX

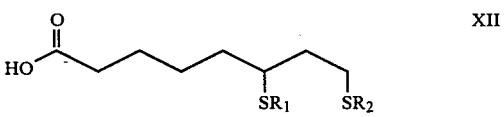

where $R_1$ and $R_2$ are hydrogen, $C_1$–$C_4$-alkyl, phenyl or benzyl, with the proviso that both $R_1$ and $R_2$ cannot be benzyl, with sodium in liquid ammonia at a temperature between −60° C. and −10° C. to form the corresponding 6,8-dimercaptooctanoic acid of formula VIII and reacting the compound of formula VIII in alkaline solutin with an iron (III) salt and oxygen to the thioctic acid of formula IX.

2. A 6,6,8-trihydrocarbyl thiooctanoic acid of formula VII

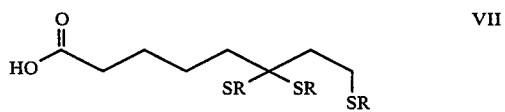

where R is $C_1$–$C_4$ alkyl, phenyl or benzyl.

3. A compound according to claim 2 where R is $C_1$–$C_4$ alkyl.

4. A process of preparing a compound of formula VI according to claim 5 comprising reacting a 2-(3-alkylthiopropionyl)-cyclopentan-1-one of formula V

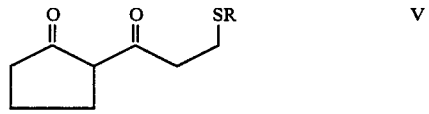

where R is $C_1$–$C_4$ alkyl in alkaline aqueous soluton at a temperature of about 20° C. to about 90° C.

5. A process of preparing a compound of formula VII according to claim 3 comprising reacting an 8-alkylthio-6-oxooctanoic acid of formula VI

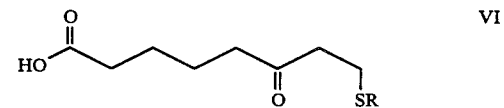

with an alkyl mercaptan at a temperature between −20° C. and 0° C.

* * * * *